(12) United States Patent
Canning et al.

(10) Patent No.: US 10,494,760 B2
(45) Date of Patent: Dec. 3, 2019

(54) METHODS AND FORMULATIONS FOR CONTROLLING HUMAN LICE INFESTATIONS

(71) Applicant: EctoGuard, LLC, Carmel, IN (US)

(72) Inventors: Peter C. Canning, Carmel, IN (US); Joseph R. Winkle, Carmel, IN (US)

(73) Assignee: EctoGuard, LLC, Carmel, IN (US)

( * ) Notice: Subject to any disclaimer, the term of this patent is extended or adjusted under 35 U.S.C. 154(b) by 0 days.

(21) Appl. No.: 16/209,672

(22) Filed: Dec. 4, 2018

(65) Prior Publication Data

US 2019/0177907 A1 Jun. 13, 2019

Related U.S. Application Data

(60) Provisional application No. 62/597,821, filed on Dec. 12, 2017.

(51) Int. Cl.
| | |
|---|---|
| *D06M 13/355* | (2006.01) |
| *A01N 45/02* | (2006.01) |
| *A01N 25/34* | (2006.01) |
| *A01N 25/14* | (2006.01) |
| *D06M 23/02* | (2006.01) |
| *A01N 25/04* | (2006.01) |

(52) U.S. Cl.
CPC .......... *D06M 13/355* (2013.01); *A01N 25/34* (2013.01); *A01N 45/02* (2013.01); *A01N 25/04* (2013.01); *A01N 25/14* (2013.01); *D06M 23/02* (2013.01); *D06M 2200/00* (2013.01)

(58) Field of Classification Search
None
See application file for complete search history.

(56) References Cited

U.S. PATENT DOCUMENTS

| | | | |
|---|---|---|---|
| 5,202,242 A | 4/1993 | Mynderse et al. | |
| 5,362,634 A | 11/1994 | Boeck et al. | |
| 5,496,932 A | 3/1996 | Mccurry, Jr. et al. | |
| 5,571,901 A | 11/1996 | Boeck et al. | |
| 5,591,606 A | 1/1997 | Turner et al. | |
| 5,631,155 A | 5/1997 | Turner et al. | |
| 6,063,771 A | 5/2000 | Snyder | |
| 2007/0299264 A1* | 12/2007 | Huang | A01N 43/10 546/281.4 |

OTHER PUBLICATIONS

DeAmicis, Carl V. et al., "Physical and Biological Properties of the Spinosyns: Novel Macrolide Pest-Control Agents from Fermentation," American Chemical Society Symposium Series: Phytochemicals for Pest Control, American Chemical Society, vol. 658, Chapter 11, p. 144-154 (1997).

Mougabure Cueto, et al., "Embryonic development of human lice: rearing conditions and susceptibility to spinosad," Mem. Inst. Oswaldo Cruz, Rio de Janeiro, vol. 101(3): 257-261 (May 2006) (6 pages).

Stough, et al., "Efficacy and safety of spinosad and permethrin creme rinses for *Pediculosis capitis* (head lice)," American Academy of Pediatrics, Pediatrics, vol. 124: 5, e389-e395 (Sep. 2009) (9 pages).

* cited by examiner

*Primary Examiner* — Celeste A Roney
(74) *Attorney, Agent, or Firm* — Koenig IP Works, PLLC

(57) ABSTRACT

Methods and formulations for controlling parasitic insect infestations, such as human lice infestations, on textiles. In one embodiment, a method includes applying an anti-parasitic formulation to a textile in need of treatment. In one embodiment, an anti-lice formulation includes an effective amount of at least one spinosyn, such as spinosad. In one embodiment, the anti-lice formulation is at least one of an aqueous suspension and an aqueous solution. The anti-lice formulation may also include one or more additional active ingredients and one or more carriers. The anti-lice formulation has parasiticidal activity when applied to a textile. For example, in one embodiment the anti-lice formulation is formulated to produce 100% adulticidal, nymphicidal, and ovicidal activity when applied to a textile in need of treatment.

16 Claims, 11 Drawing Sheets

300

Start

Add an amount of spinosyn to a non-organic carrier to produce at least one of an aqueous suspension and an aqueous solution in which the spinosyn is present in a concentration of approximately 1000 ppm — 302

End

*FIG. 3*

| spinosad Concentration | EGG VIABILITY PER DAY | | | | | | TOTAL | % HATCHABILITY |
|---|---|---|---|---|---|---|---|---|
| | 7 | 8 | 9 | 10 | 11 | 12 | | |
| 1000ppm | 0 | 1 | 2 | 2 | 3 | 0 | 8/20 | 40 |
| 500ppm | 0 | 0 | 1 | 2 | 3 | 0 | 6/19 | 32 |
| 250ppm | 0 | 2 | 3 | 3 | 2 | 0 | 10/11 | 91 |
| ddH$_2$O | 0 | 2 | 5 | 3 | 0 | 0 | 10/10 | 100 |

Study 1: Impact of various concentrations of spinosad upon lice egg viability

*FIG. 4*

| | DAY | | | | | | | |
|---|---|---|---|---|---|---|---|---|
| | 1 | 2 | 3 | 4 | 5 | 6 | | |
| spinosad Concentration | LICE (ADULT) MORTALITY | | | | | | TOTAL | % MORTALITY |
| 1000ppm | 5 | 5 | - | - | - | - | 10/10 | 100 |
| 500ppm | 3 | 7 | - | - | - | - | 10/10 | 100 |
| 250ppm | 2 | 8 | - | - | - | - | 10/10 | 100 |
| water | 0 | 2 | 3 | 2 | 2 | 0 | 9/10 | 90 |
| | | | | | | | | |
| Spinosad Concentration | LICE (IMMATURE) MORTALITY | | | | | | TOTAL | % MORTALITY |
| 1000ppm | 8 | 2 | - | - | - | - | 10/10 | 100 |
| 500ppm | 8 | 2 | - | - | - | - | 10/10 | 100 |
| 250ppm | 6 | 4 | - | - | - | - | 10/10 | 100 |
| water | 0 | 0 | 2 | 2 | 4 | 0 | 8/10 | 80 |

Study 1: Impact of various concentrations of spinosad on adult and immature lice viability

*FIG. 5*

| Treatment | Exposure time (min) |
|---|---|
| CONSERVE® (1000 ppm spinosad) | 10 |
| NIX® (positive control) | 10 |
| ddH$_2$O (negative control) | 10 |

Study 2: Treatments and exposure times

*FIG. 6*

| # OF EGGS | Treatment | DAYS POST-TREAMENT | 7 | 8 | 9 | 10 | 11 | TOTAL | % HATCHABILITY |
|---|---|---|---|---|---|---|---|---|---|
| 30 | spinosad 1000 ppm | # OF EGGS HATCHED | 0 | 0 | 0 | 0 | 0 | 0/30 | 0 |
| 49 | water (negative control) | | 3 | 19 | 22 | 2 | 3 | 49/49 | 100 |
| 60 | NIX® (positive control) | | 0 | 0 | 8 | 23 | 0 | 31/60 | 51.7 |

Study 2: Ovicidal action of an anti-lice formulation having 1000ppm spinosad versus a positive control and a negative control

*FIG. 7*

| TREATMENT [ ] | DAYS POST-TREATMENT | 1 | 2 | 3 | 4 | 5 | 6 | 7 | 8 | 9 | 10 | 11 | TOTAL | % MORT-ALITY |
|---|---|---|---|---|---|---|---|---|---|---|---|---|---|---|
| spinosad 1000ppm | DEAD LICE (ADULT) | 30 | - | - | - | - | - | - | - | - | - | - | 30/30 | 100 |
| water (negative control) | | 0 | 0 | 0 | 0 | 0 | 1 | 1 | 1 | 1 | 1 | 1 | 6/30 | 20 |
| NIX® (positive control) | | 15 | 0 | 1 | 0 | 0 | 1 | 1 | 0 | 1 | 1 | 0 | 20/30 | 66.7 |
| spinosad 1000ppm | DEAD LICE (IMMATURE) | 30 | - | - | - | - | - | - | - | - | - | - | 30/30 | 100 |
| water (negative control) | | 0 | 0 | 0 | 0 | 1 | 1 | 0 | 0 | 0 | 0 | 0 | 2/30 | 6.7 |
| NIX® (positive control) | | 20 | 4 | 2 | 1 | 0 | 0 | 0 | 0 | 0 | 0 | 0 | 27/30 | 90 |

Study 2: Adulticidal or larvicidal action of an anti-lice formulation having 1000ppm spinosad versus a positive control and a negative control

*FIG. 8*

| Minutes (min) | Hours (h) | LICE MORTALITY (TREATED) | | | | LICE MORTALITY (CONTROL) | | | |
|---|---|---|---|---|---|---|---|---|---|
| | | ADULT n=15 | | IMMATURE n=15 | | ADULT n=15 | | IMMATURE n=15 | |
| | | DEAD | KNOCKDOWN | DEAD | KNOCKDOWN | DEAD | KNOCKDOWN | DEAD | KNOCKDOWN |
| 0 | 0 | 0 | 0 | 0 | 0 | 0 | 0 | 0 | 0 |
| 15 | 0.25 | 0 | 0 | 0 | 0 | 0 | 0 | 0 | 0 |
| 30 | 0.50 | 0 | 3 | 0 | 0 | 0 | 0 | 0 | 0 |
| 45 | 0.75 | 0 | 6 | 0 | 3 | 0 | 0 | 0 | 0 |
| 60 | 1.00 | 0 | 12 | 0 | 6 | 0 | 0 | 0 | 0 |
| 75 | 1.25 | 0 | 15 | 0 | 15 | 0 | 0 | 0 | 0 |
| 90 | 1.50 | 0 | 15 | 0 | 15 | 0 | 0 | 0 | 0 |
| 105 | 1.75 | 0 | 15 | 0 | 15 | 0 | 0 | 0 | 0 |
| 120 | 2.00 | 0 | 15 | 0 | 15 | 0 | 0 | 0 | 0 |
| 135 | 2.25 | 0 | 15 | 0 | 15 | 0 | 0 | 0 | 0 |
| 150 | 2.50 | 0 | 15 | 0 | 15 | 0 | 0 | 0 | 0 |
| 165 | 2.75 | 0 | 15 | 0 | 15 | 0 | 0 | 0 | 0 |
| 180 | 3.00 | 0 | 15 | 0 | 15 | 0 | 0 | 0 | 0 |
| 195 | 3.25 | 0 | 15 | 0 | 15 | 0 | 0 | 0 | 0 |
| 210 | 3.50 | 0 | 15 | 0 | 15 | 0 | 0 | 0 | 0 |
| 225 | 3.75 | 0 | 15 | 0 | 15 | 0 | 0 | 0 | 0 |
| 240 | 4.00 | 0 | 15 | 0 | 15 | 0 | 0 | 0 | 0 |
| 255 | 4.25 | 0 | 15 | 0 | 15 | 0 | 0 | 0 | 0 |
| 270 | 4.50 | 0 | 15 | 0 | 15 | 0 | 0 | 0 | 0 |
| 285 | 4.75 | 0 | 15 | 0 | 15 | 0 | 0 | 0 | 0 |
| 300 | 5.00 | 0 | 15 | 0 | 15 | 0 | 0 | 0 | 0 |
| 315 | 5.25 | 0 | 15 | 0 | 15 | 0 | 0 | 0 | 0 |
| 330 | 5.50 | 1 | 14 | 0 | 15 | 0 | 0 | 0 | 0 |
| 345 | 5.75 | 0 | 14 | 0 | 15 | 0 | 0 | 0 | 0 |
| 360 | 6.00 | 0 | 14 | 1 | 14 | 0 | 0 | 0 | 0 |
| 375 | 6.25 | 0 | 14 | 0 | 14 | 0 | 0 | 0 | 0 |
| 390 | 6.50 | 0 | 14 | 0 | 14 | 0 | 0 | 0 | 0 |
| 405 | 6.75 | 5 | 9 | 0 | 14 | 0 | 0 | 0 | 0 |
| 420 | 7.00 | 4 | 5 | 2 | 12 | 0 | 0 | 0 | 0 |
| 435 | 7.25 | 0 | 5 | 0 | 12 | 0 | 0 | 0 | 0 |
| 450 | 7.50 | 0 | 5 | 1 | 11 | 0 | 0 | 0 | 0 |
| 1020 | 17.00 | 15 | 0 | 15 | 0 | 2 | 0 | 0 | 0 |

*FIG. 9*

| Minutes (min) | Hours (h) | LICE MORTALITY (TREATED) | | | | LICE MORTALITY (CONTROL) | | | |
|---|---|---|---|---|---|---|---|---|---|
| | | ADULT n = 15 | | IMMATURE n = 15 | | ADULT n = 15 | | IMMATURE n = 15 | |
| | | DEAD | KNOCKDOWN | DEAD | KNOCKDOWN | DEAD | KNOCKDOWN | DEAD | KNOCKDOWN |
| 0 | 0 | 0% | 0% | 0% | 0% | 0% | 0% | 0% | 0% |
| 15 | 0.25 | 0% | 0% | 0% | 0% | 0% | 0% | 0% | 0% |
| 30 | 0.50 | 0% | 20% | 0% | 0% | 0% | 0% | 0% | 0% |
| 45 | 0.75 | 0% | 40% | 0% | 20% | 0% | 0% | 0% | 0% |
| 60 | 1.00 | 0% | 80% | 0% | 40% | 0% | 0% | 0% | 0% |
| 75 | 1.25 | 0% | 100% | 0% | 100% | 0% | 0% | 0% | 0% |
| 90 | 1.50 | 0% | 100% | 0% | 100% | 0% | 0% | 0% | 0% |
| 105 | 1.75 | 0% | 100% | 0% | 100% | 0% | 0% | 0% | 0% |
| 120 | 2.00 | 0% | 100% | 0% | 100% | 0% | 0% | 0% | 0% |
| 135 | 2.25 | 0% | 100% | 0% | 100% | 0% | 0% | 0% | 0% |
| 150 | 2.50 | 0% | 100% | 0% | 100% | 0% | 0% | 0% | 0% |
| 165 | 2.75 | 0% | 100% | 0% | 100% | 0% | 0% | 0% | 0% |
| 180 | 3.00 | 0% | 100% | 0% | 100% | 0% | 0% | 0% | 0% |
| 195 | 3.25 | 0% | 100% | 0% | 100% | 0% | 0% | 0% | 0% |
| 210 | 3.50 | 0% | 100% | 0% | 100% | 0% | 0% | 0% | 0% |
| 225 | 3.75 | 0% | 100% | 0% | 100% | 0% | 0% | 0% | 0% |
| 240 | 4.00 | 0% | 100% | 0% | 100% | 0% | 0% | 0% | 0% |
| 255 | 4.25 | 0% | 100% | 0% | 100% | 0% | 0% | 0% | 0% |
| 270 | 4.50 | 0% | 100% | 0% | 100% | 0% | 0% | 0% | 0% |
| 285 | 4.75 | 0% | 100% | 0% | 100% | 0% | 0% | 0% | 0% |
| 300 | 5.00 | 0% | 100% | 0% | 100% | 0% | 0% | 0% | 0% |
| 315 | 5.25 | 0% | 100% | 0% | 100% | 0% | 0% | 0% | 0% |
| 330 | 5.50 | 7% | 93% | 0% | 100% | 0% | 0% | 0% | 0% |
| 345 | 5.75 | 7% | 93% | 0% | 100% | 0% | 0% | 0% | 0% |
| 360 | 6.00 | 7% | 93% | 7% | 93% | 0% | 0% | 0% | 0% |
| 375 | 6.25 | 7% | 93% | 7% | 93% | 0% | 0% | 0% | 0% |
| 390 | 6.50 | 7% | 93% | 7% | 93% | 0% | 0% | 0% | 0% |
| 405 | 6.75 | 40% | 60% | 7% | 93% | 0% | 0% | 0% | 0% |
| 420 | 7.00 | 67% | 33% | 20% | 80% | 0% | 0% | 0% | 0% |
| 435 | 7.25 | 67% | 33% | 20% | 80% | 0% | 0% | 0% | 0% |
| 450 | 7.50 | 67% | 33% | 27% | 73% | 0% | 0% | 0% | 0% |
| 1020 | 17.00 | 100% | 0% | 100% | 0% | 13% | 0% | 0% | 0% |

*FIG. 10*

| EGG HATCHABILITY (TREATED) || EGG HATCHABILITY (CONTROL) ||
|---|---|---|---|
| Day | Hatched | Day | Hatched |
| 1 | 0 | 1 | 0 |
| 2 | 0 | 2 | 0 |
| 3 | 0 | 3 | 0 |
| 4 | 0 | 4 | 0 |
| 5 | 0 | 5 | 0 |
| 6 | 0 | 6 | 0 |
| 7 | 0 | 7 | 9 |
| 8 | 0 | 8 | 21 |
| 9 | 0 | 9 | 0 |
| 10 | 0 | 10 | 0 |
| TOTAL: | 0 | TOTAL: | 30 |
| n = | 56 | n = | 40 |

| % HATCHABILITY ||
|---|---|
| TREATED: | 0% |
| CONTROL: | 75% |

*FIG. 12*

METHODS AND FORMULATIONS FOR CONTROLLING HUMAN LICE INFESTATIONS

CROSS-REFERENCE TO RELATED APPLICATION

This application is related to and claims priority to U.S. Provisional Application Ser. No. 62/597821, filed Dec. 12, 2017, the entirety of which is incorporated herein by reference.

FIELD

The present technology is generally related to the control of ectoparasites such as human lice.

BACKGROUND

The sucking lice, or Anoplura (Order Phthiraptera, Suborder Anoplura), are parasitic insects found on nearly all groups of mammals. Of the 15 recognized families of Anoplura, two families, Pediculidae and Pthiridae, have species which infest humans. These human lice are: the head louse, *Pediculus humanus capitis*; the body or clothing louse, *Pediculus humanus humanus*, sometimes called *Pediculus corporis*; and the crab louse, *Pthirus pubis*. These human lice have bodies that are constructed of a hard chitinous exoskeleton, like all insects, and are very small (about 2-3 mm in length). The human lice are prolific egg (ova) layers, and they typically deposit eggs either on a hair or fabric fiber and attach them firmly with a cement-like excretion. Nymphs hatch from the eggs in about six to ten days, depending on temperature. The empty shells remaining after the nymphs emerge from the eggs look like white grains of sand, and these shells are called nits.

Infestation of the human body by lice is an increasingly prevalent social and health problem in many countries, including the United States (US). Head lice affect as many as 6-12 million people each year globally. The problem is particularly prevalent in preschool and elementary-age children (aged 3-10) and their families. Head lice infestation typically causes itching of the scalp. As the lice feed on human blood, they may cause lesions to develop on the scalp, swollen glands on the neck or under arms, or other symptoms. Head lice infestation also causes serious problems due to the negative social implications of the infestation. Head lice infestations are believed to account for 12 million to 24 million missed school days a year in the US. A majority of US public schools have instituted a no-lice, or a no-lice and no-nit policy, forcing absenteeism on children and requiring working parents to stay at home to look after them or provide other arrangements for child care. For example, see Burkhart and Burkhart (2006, Expert Opin. Drug Saf. 5(1):169-179) for a review.

Body lice (*Pediculus humanus humanus* and *Pthirus pubis*) are also troublesome for humans. In addition to the problems caused by head lice, body lice carry the additional hazard of being the vectors of certain diseases, such as exanthematic or epidemic typhus and recurrent fever.

The louse's hard chitinous exoskeleton serves as protection from dehydration and external elements and also resists insecticides and other treatments, making control difficult. Additionally, lice eggs are protected by a surrounding hard keratin sheath. Although lice may be more readily affected by the use of an insecticide, the eggs often remain resistant to such attack. Thus, treatment of a lice infestation may necessitate both a pediculicide, which kills the adult lice, and an ovicide, which interrupts the development of the eggs.

Biologically active agents, such as avermectins (such as ivermectin), organophosphates (such as malathion), organochlorines (such as lindane and gammabenzene hexachloride), pyrethrins, and synthetic pyrethroids (such as permethrin), have been used for some time in attempts to control lice. Each of these agents, however, has drawbacks. For example, lindane has a relatively poor safety profile. Natural pyrethrin requires frequent follow-up treatments because it provides only short-term residual action. Synthetic pyrethroids, although more effective against lice than natural pediculicides, are often more toxic to the subject being treated. In addition, resistance is an issue with such agents. Newer recent classes such as avermectins (such as ivermectin) are as yet unproven in their head lice control effectiveness in patients.

Pyrethrins are any one of six naturally occurring insecticides extracted from the chrysanthemum flower. Along with its synthetic derivative, permethrin, these molecules act on susceptible head lice by increasing sodium levels in the nervous system of the lice. The increased sodium levels cause membrane depolarization in the nervous system, which eventually leads to spastic paralysis and death of the head lice. When first introduced, both pyrethrin and permethrin were highly effective at eliminating susceptible lice. In the late 1980s, various formulations of both active ingredients had a high efficacy for eliminating adult head lice and their nits. However, recent reports indicate that treatment-resistant strains of head lice have evolved for popular commercial products including NIX® (INSIGHT Pharmaceuticals, LLC., Tarrytown, N.Y.), which has 1% permethrin as an active ingredient, and various RID® (Bayer HealthCare LLC, Pittsburgh, Pa.) products, which have approximately 0.33% pyrethrin as an active ingredient. Given the prevalence and popularity of these products, it comes as no surprise that strains of treatment-resistant head lice have been identified in both the US and Europe due to the similar killing pathway for both insecticides.

Human lice reinfestation can occur via materials or certain surfaces that come into contact with humans, such as clothing, bedding, couches, chairs, blankets, and other fabric-based accessories such as hats, stuffed animals, towels, throw pillows, and the like. While mature adult lice may not be able to survive without a host longer than two days or so, eggs (which take around seven days to hatch) may be firmly cemented to clothing, fabric, bedding, and other fabrics that could contact human skin. Currently known methods of combatting such reinfestation include subjecting clothing, bedding, and fabrics to certain treatments, including exposing the textiles to excessive heat in a dryer, and placing the fabrics in plastic bags to which a vacuum can be applied to create a type of anaerobic environment that suffocates and even desiccates the lice. However, it is not always possible to use these methods on larger items, such as couches or car seats, and in some cases performing these methods may cross-contaminate other non-target items with lice.

SUMMARY

The techniques of this disclosure generally relate to formulations and methods for controlling a lice infestation, such as a human lice infestation. In one embodiment, a method of controlling an infestation of parasitic insects comprises applying an anti-lice formulation to a textile, the anti-lice formulation including an effective amount of a spinosyn an a non-organic carrier. Further, in one embodiment the anti-lice formulation is applied to, and is allowed to remain on, a textile (that is, the anti-lice formulation is not washed off or removed from the textile). Still further, in one embodiment the anti-lice formulation is configured such that allowing it to remain on the textile does not compromise the integrity of the textile (for example, the anti-lice formulation does not cause degradation of the textile and does not alter the color or composition of the textile).

In one aspect of the embodiment, the spinosyn is at least one of a spinosad, a physiologically acceptable salt of a spinosyn, and a physiologically acceptable derivative of a spinosyn.

In one aspect of the embodiment, the anti-lice formulation further includes at least one additional active ingredient, the at least one additional active ingredient being at least one of other spinosyns, synthetic pyrethroids, natural pyrethins, organophosphates, organochlorines, carbamates, foramidines, avermectins, milbemycins, isoxazolines, insect growth regulators, nitromethylenes, pyridines, and pyrazoles.

In one aspect of the embodiment, the anti-lice formulation is a liquid formulation, the liquid formulation being at least one of an aqueous solution and an aqueous suspension, applying the anti-lice formulation to the textile includes spraying the anti-lice formulation onto the textile in need of treatment.

In one aspect of the embodiment, the anti-lice formulation is a wettable powder, and the method further comprises mixing the wettable powder with a liquid non-organic carrier before applying the anti-lice formulation to the textile.

In one aspect of the embodiment, the anti-lice formulation is a concentrate formulation including spinosyn in a concentration of greater than 1000 ppm, the method further comprising: diluting the concentrate formulation with a liquid non-organic carrier to a spinosyn concentration of approximately 1000 ppm before applying the anti-lice formulation to the textile.

In one aspect of the embodiment, the effective amount of spinosyn is present in the anti-lice formulation in an amount of from approximately 50 ppm to approximately 5000 ppm. In one aspect of the embodiment, the effective amount of spinosyn is from approximately 250 to approximately 1000 ppm.

In one aspect of the embodiment, the infestation of parasitic insects is an infestation of at least one of *Pediculus humanus capitis, Pediculus humanus humanus*, and *Pthirus pubis*.

In one aspect of the embodiment, the textile is a textile in need of treatment, the textile in need of treatment including at least one of natural fibers and synthetic fibers.

In one aspect of the embodiment, the method further comprises, after applying the anti-lice formulation to the textile: allowing the anti-lice formulation to dry on the textile without removing the anti-lice formulation from the textile.

In one embodiment, an anti-lice formulation comprises: an effective amount of spinosyn; and a non-organic carrier, the anti-lice formulation being one of a suspension and a solution.

In one aspect of the embodiment, the anti-lice formulation is configured to be applied to a textile in need of treatment and to dry on the textile in need of treatment without changing a quality of the textile in need of treatment. In one aspect of the embodiment, the textile in need of treatment includes at least one of natural fibers and synthetic fibers.

In one aspect of the embodiment, the spinosyn is at least one of a spinosad and a physiologically acceptable salt of a spinosyn.

In one aspect of the embodiment, the anti-lice formulation further comprises further comprising at least one additional active ingredient, the at least one additional active ingredient is selected from the group consisting of other spinosyns, synthetic pyrethroids, natural pyrethins, organophosphates, organochlorines, carbamates, foramidines, avermectins, milbemycins, isoxazolines, insect growth regulators, nitromethylenes, pyridines, and pyrazoles.

In one aspect of the embodiment, the anti-lice formulation is a liquid formulation, the liquid formulation being one at least one of an aqueous suspension and an aqueous solution.

In one aspect of the embodiment, the anti-lice formulation is at least one of a wettable powder, a gel, a paste, a lotion, a foam, and a spray.

In one aspect of the embodiment, the effective amount of spinosyn is present in the anti-lice formulation in an amount from about 250 to about 1000 ppm.

In one embodiment, a method of producing an anti-lice formulation comprises: adding an amount of spinosyn to a non-organic carrier to produce at least one of an aqueous suspension and an aqueous solution in which the spinosyn is present in a concentration of approximately 1000 ppm.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is a flowchart of an exemplary method of producing an anti-lice formulation in accordance with the present disclosure;

FIG. 4 is a chart showing an exemplary impact of various concentrations of an anti-lice formulation on lice egg viability in an exemplary first study;

FIG. 5 is a chart showing an exemplary impact of various concentrations of an anti-lice formulation on adult and immature lice viability in the exemplary first study;

FIG. 6 is a chart showing exemplary treatments and exposure times used in an exemplary second study;

FIG. 7 is a chart showing an exemplary impact of an anti-lice formulation according to the present disclosure versus water (negative control) and a positive control formulation on lice egg viability in the exemplary second study;

FIG. 8 is a chart showing an exemplary impact of an anti-lice formulation according to the present disclosure versus water (negative control) and a positive control formulation on mortality responses for adult and immature lice over 11 days post-treatment in the exemplary second study;

FIG. 9 is a chart showing an exemplary impact of an anti-lice formulation according to the present disclosure versus a negative control on adult and immature lice mortality responses in an exemplary third study;

FIG. 10 is a chart showing an exemplary impact of an anti-lice formulation according to the present disclosure versus the negative control used in FIG. 9 on adult and immature lice mortality responses in the exemplary third study;

FIG. 12 is a chart showing hatchability of eggs following spray application of both an anti-lice formulation according to the present disclosure (treated) and deionized water (negative control) to a fabric in the exemplary third study.

DETAILED DESCRIPTION

Figure 1:
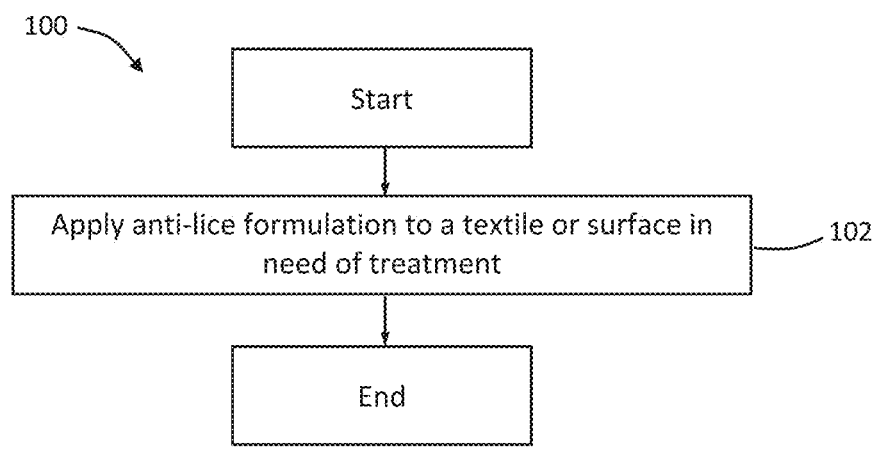
FIG. 1 is a flowchart of an exemplary method of controlling lice, such as human lice in accordance with the present disclosure.

Before describing in detail exemplary embodiments, it is noted that the embodiments reside primarily in combinations of formulations and method steps related to controlling an infestation of parasitic insects, for example, human lice, on a textile. In one embodiment, the present disclosure relates to an anti-lice formulation containing at least one active ingredient sufficient to control an infestation of lice when applied directly to a textile or surface, rather than to a human, in which the lice infestation is located. In one embodiment, the lice are human lice such as Anoplura. The present disclosure also relates to a method of applying an anti-lice formulation to a textile or surface to control a human lice infestation. In one embodiment, as discussed below, the anti-lice formulation includes at least one spinosyn, or a physiologically acceptable derivative or salt thereof. Further, in one embodiment, the anti-lice formulation also includes an acceptable carrier.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

As used herein, the term "spinosyn" refers to an individual spinosyn factor (A, B, C, D, E, F, G, H, J, K, L, M, N, O, P, Q, R, S, T, U, V, W, or Y), a physiologically acceptable derivative of a spinosyn factor, such as an N-demethyl derivative of an individual spinosyn factor, a physiologically acceptable salt of a spinosyn factor, and/or any combination thereof. Further, the term "spinosyn" as used herein in the singular does not necessarily mean only one spinosyn factor and may include more than one spinosyn factor, as well as combinations of spinosyn factors and physiologically acceptable derivatives and/or physiologically acceptable salts thereof. Further, the term "spinosyns" as used herein refers to one or more spinosyn factor.

Spinosyns are naturally derived fermentation products. They are macrolides produced by cultivation of *Saccharopolyspora spinosa*, a species of bacteria. The fermentation produces multifactors, including spinosyn A and spinosyn D (also called A83543A and A83543D), which are the two spinosyns that are most active as insecticides. A product comprised mainly of these two spinosyns (approximately 85% A and 15% D) is available commercially under the name spinosad. The name "spinosad" comes from a contraction of the spinosyns "A" and "D". U.S. Pat. No. 6,063,771 describes spinosyns and is incorporated herein by reference.

Each spinosyn factor has a 12-membered macrocyclic ring that is part of an unusual tetracyclic ring system to which two different sugars are attached: the amino-sugar forosamine and the neutral sugar 2N,3N,4N-tri-O-methylrhamnose. This unique structure sets spinosyns apart from other macrocyclic compounds.

Spinosyn A (A83543A) was the first spinosyn isolated and identified from the fermentation broth of *Saccharopolyspora spinosa*. Subsequent examination of the fermentation broth revealed that the parent strain of *S. spinosa* produced other spinosyns that have been labeled A to J (A83543A to J). Compared to spinosyn A, spinosyns B-J are characterized by differences in the substitution patterns on the amino group of the forosamine, at selected sites on the tetracyclic ring system and on 2N,3N,4N-tri-O-methylrhamnose. The strains of *S. spinosa* currently in use produce a mixture of spinosyns, of which the primary components are spinosyn A (about 85%) and spinosyn D (about 15%). Additional spinosyns, lettered from K to W, have been identified from mutant strains of *S. spinosa*.

Boeck et al. described spinosyns A-H and J (which they called A83543 factors A, B, C, D, E, F, G, H and J), and salts thereof, in U.S. Pat. No. 5,362,634 (issued Nov. 8, 1994); U.S. Pat. No. 5,496,932 (issued Mar. 5, 1996); and U.S. Pat. No. 5,571,901 (issued Nov. 5, 1996). Mynderse et al. described spinosyns L-N (which they called A83543 factors L, M and N), their N-demethyl derivatives, and salts thereof, in U.S. Pat. No. 5,202,242 (issued Apr. 13, 1993); and Turner et al. described spinosyns Q-T (which they called A83543 factors Q, R, S and T), their N-demethyl derivatives, and salts thereof, in U.S. Pat. No. 5,591,606 (issued Jan. 7, 1997) and U.S. Pat. No. 5,631,155 (issued May 29, 1997). These patents are incorporated herein by reference. Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146-154 (1997).

The spinosyns can react to form salts, and salts that are physiologically acceptable (referred to herein as "physiologically acceptable salts") are also useful in the formulations and methods in accordance with the present disclosure. Such salts are prepared using standard procedures for salt preparation. For example, spinosyn A can be neutralized with an appropriate acid to form an acid additional salt. In one embodiment, the acid addition salts of spinosyns are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

In addition to the spinosyn, the methods and formulations of the present disclosure may optionally further include one or more other compounds that have activity against lice (for example, human lice) such as, for example, other spinosyns, synthetic pyrethroids, natural pyrethins, organophosphates, organochlorines, carbamates, foramidines, avermectins, milbemycins, isoxazolines, insect growth regulators (including chitin synthesis inhibitors, juvenile hormone analogs, and juvenile hormones), nitromethylenes, pyridines and pyrazoles.

As used herein, the terms "formulation" and "anti-lice formulation" mean a mixture or compound that contains an effective amount of active ingredient (such as spinosyn in general, or spinosad in particular), either alone or in combination with one or more of the other types of compounds listed above, formulated into a product suitable for application to a textile. The formulations of the present invention are suitable for direct application to textiles which have, or are believed to have, a human lice infestation therein or thereon. Such formulations include, but are not limited to, liquids, gels, pastes, lotions, foams, sprays, and powders (such as wettable powders) containing the active component or components (for example, spinosyn in general, or spinosad in particular). In some embodiments, such formulations include a physiologically acceptable carrier.

As used herein, the terms "carrier" and "physiologically acceptable carrier" describe any ingredient, other than the active component(s) in a formulation, that is a primary ingredient, that is, that makes up at least a threshold amount of the anti-lice formulation. In one embodiment, the threshold amount is 25% and the carrier makes up at least 25% of the anti-lice formulation. Further, in one embodiment the carrier is a fluid ingredient in which spinosyn is at least partially soluble and/or appropriately suspended, but that is not reasonably expected to affect the integrity of the textile or surface to which it is applied. In one embodiment, the carrier is water. Thus, "harsh" organic solvents such as dimethyl sulfoxide (DMSO), N-methyl-2-pyrrolidone (NMP), petroleum distillates, acetates, ketones, or the like are not preferred. As used herein, the terms "additive" or "secondary ingredients" include ingredients that may be present in the carrier and the anti-lice formulation, but that make up less than a threshold amount of the anti-lice formulation. In one embodiment, the threshold amount is 25% and the additive(s) make up less than 25% of the anti-lice formulation. Like the carrier(s), in some embodiments the additive(s) are also not "harsh" organic solvents, or at least are not included in the anti-lice formulation in concentrations or amounts that would reasonably be expected to affect the textile's integrity. For example, some commercially available anti-lice preparations such as those formulated for application to hair or skin include organic solvents and must be washed or rinsed away after a certain amount of time. However, these formulations are not suitable for application to a textile, particularly if the formulation is not washed, rinsed, or otherwise removed from the textile, as they may affect the integrity and color of the textile. It is contemplated that in some embodiments the anti-lice formulation of the present disclosure may include one or more carriers or additives or other secondary ingredients that are "weak" organic solvents or solubilizing agents that are at least partially miscible in water and that are not (or are not included in concentrations that are) reasonably expected to affect the textile's integrity. These "weak" organic solvents may include but are not limited to propylene glycol, small-chain aromatic or aliphatic alcohols, surfactants, or the like. For example, such "weak" organic solvents may be added to the anti-lice formulation (or may be included in the concentrate formulation and some amount may remain in the anti-lice formulation when the concentrate formulation is diluted) to enhance or improve certain qualities of the anti-lice formulation such as the solubility of spinosyn, suspension of spinosyn, temperature stability, spray properties, wetting properties, reduction or elimination of crystallization, or the like. Thus, in some embodiments the anti-lice formulation is referred to as having a non-organic carrier as a primary ingredient, even if some small amounts of organic additives are present, as long as the organic additives are not reasonably expected to affect the textile's integrity. In some embodiments, the choice of carrier(s) and additive(s) will depend on, for example, factors such as the particular anti-lice formulation being used, the active ingredient(s), the effect of the carrier on solubility and stability, and the nature or form of the anti-lice formulation.

In some embodiments, the anti-lice formulations include wettable powder formulations having from about 1% to about 80% active ingredient (for example, spinosyn or spinosad) by weight. In some embodiments, the anti-lice formulation is formulated as diluted suspensions (such as aqueous suspensions) and/or as diluted solutions (such as aqueous solutions). For example, the spinosyn(s) may be present in an anti-lice formulation in an amount or concentration of about 1 ppm (or 0.0001% by weight) to about 10,000 ppm (or 1% by weight), from about 50 ppm (or 0.005% by weight) to about 5,000 ppm (or 0.05% by weight), from about 100 ppm (or 0.01% by weight) to about 2500 ppm (or 0.25% by weight), and from about 250 ppm (or 0.25% by weight) to about 1000 ppm (or 0.1% by weight). Further, in some embodiments the anti-lice formulation is a pre-diluted formulation (referred to herein as a "ready-to-use" anti-lice formulation). In one non-limiting example, spinosyn or spinosad is present in a concentrate formulation in an amount of from approximately 2.5% to approximately 44.2% by weight of active ingredient. In some embodiments, the concentrate formulations of the present disclosure are from approximately 0.5% to approximately 45%, including 44.2%, by weight of active ingredient. In one embodiment, the concentrate formulation is then diluted to create a ready-to-use anti-lice formulation, such as a diluted aqueous suspension and/or diluted aqueous solution. In one embodiment, the concentrate formulation is diluted with water or other carrier fluid until the active ingredient (for example, spinosyn or spinosad) is present in the resulting ready-to-use anti-lice formulation in a concentration of approximately 1000 ppm (for example, 1000 ppm±200 ppm). Thus, the anti-lice formulation may be sold to a retailer or end-user as either a concentrate formulation that is to be diluted before use or as a ready-to-use formulation that can be applied to a textile without further preparation (other than, in some circumstances, shaking or agitation to re-suspend any solid particles).

In one embodiment, the spinosyn is either completely or partially soluble based on the concentration in water having a pH of 6.5 to 7. Use of organic acids such as citric acid, tartaric acid, acetic acid, and combinations thereof, may be employed to increase the spinosyn solubility.

In some embodiments, primarily non-ionic surfactants at levels of 0.05% to 0.1% may also be used in an anti-lice formulation to aid in solubilizing a spinosyn in an aqueous environment. Nonionic surfactants include the primary and secondary alcohol ethoxylates, especially the $C_8$-$C_{20}$ aliphatic alcohols ethoxylated with an average of from 1 to 20 moles of ethylene oxide per mole of alcohol, and more especially the $C_{10}$-$C_{15}$ primary and secondary aliphatic alcohols ethoxylated with an average of from 1-10 moles of ethylene oxide per mole of alcohol. Non-ethoxylated nonionic surfactants include alkylpolyglycosides, glycerol monoethers, and polyhydroxyamides (glucamide). Water-miscible vehicles may be employed, and include ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, dimethyl sulfoxide, benzyl alcohol, and isopropanol. Other additives may be included such as anionic surfactants; xanthan gum, gum Arabic, or any other suitable viscosity builder; inorganic salts such as magnesium or aluminum carbonates; glycol or propylene glycol as a freeze point depression agent; an antimicrobial agent; in some cases an ionic or neutral dispersant. However, as noted above, in some embodiments the additives are not "harsh" organic solvents, or are not "harsh" organic solvents included in a concentration, that are reasonably expected to affect or adversely affect the integrity of the textile or surface to which they are applied.

As used herein, the phrase "lice infestation" means the presence of at least one louse, in one or more of the louse's life stages. In one embodiment, the lice infestation is a human lice infestation, in which case the lice infestation is referred to as a "human lice infestation." However, it will be understood that reference to human lice used herein may also include other species of lice or other parasites, including human ectoparasites. The human lice infestation may be present within or on a textile, fabric, or other surface to which the human lice may cling or be attached. Further, although human lice do not typically survive on other types of surfaces without a host for any appreciable amount of time and do not typically deposit eggs on such surfaces (thus reducing or eliminating the need to control the human lice population on such surfaces), the anti-lice formulation may also be applied to non-textile surfaces, if desired, such as porous and semi-porous surfaces (for example, wood, plaster, granite, stone, and concrete) as well as nonporous surfaces, such as plastics, vinyl, glass, or the like.

As used herein, the phrases "controlling a human lice infestation" and "controlling a lice infestation" mean the prevention of parasitic insect infestations, such as human lice infestations and/or the treatment of existing parasitic insect infestations, such as human lice infestations. Furthermore, as used herein the phrases "controlling a human lice infestation" and "controlling a lice infestation" include preventing, minimizing, and/or eliminating an infestation by parasitic insects such as human lice. In some embodiments, the human lice are present at at least one life stage selected from the group consisting of egg, larvae, and adult. Further, the phrases "controlling a human lice infestation" and "controlling a lice infestation" include infestations and reinfestations, such as infestations and/or reinfestations of textiles.

As used herein, the terms "effective amount" and "ectoparasiticidal amount" refer to the amount of active ingredient (for example, spinosyn) needed for a certain time (which may be referred to herein as exposure time) to control the parasitic insect infestation, such as a human lice infestation. It will be understood that the active ingredient amounts and exposure times will vary depending upon a number of factors. For example, the duration of time for which the spinosyn is contact with human lice (exposure time) may be about 5 minutes to about 24 hours or more, about 30 minutes to about 12 hours, and about 60 minutes to about 6 hours. Also, in some embodiments, the textile is saturated with a formulation to assure contact with the human lice when a liquid formulation is used. However, it will be understood that the methods and formulations will be effective in amounts which do not saturate the textile.

As used herein, the term "textile" includes any material or surface which is designed to come in contact with, or is capable of coming into contact with, humans and is capable of supporting a human lice infestation in one or more of the lice's life stages. As used herein, the phrases "textile in need thereof," "textile to be treated," and "textile in need of treatment" mean a textile that has, is believed to have, or could have, a human lice infestation therein or thereon. Textiles suitable for treatment with one or more anti-lice formulations in accordance with the present disclosure include textiles composed of natural and/or synthetic fibers, as well as textile blends in woven or non-woven form, such as knit goods, yarns or fibers, and which come in contact with humans (or are capable of coming into contact with humans) and which contain or are capable of containing one or more human lice at one or more stages of life. Natural fibers include but are not limited to cotton, wool, silk, jute, and hemp. Synthetic fibers include but are not limited to polyamides, polyesters, polyacryl nitrites, polyolefins (for example, polypropylene or polyethylene), TEFLON®, and/or mixtures of fibers, for example mixtures of synthetic and natural fibers. Textiles may be in form of coverings, for example, bedclothes, mattresses, pillows, duvets, cushions and throw pillows, curtains, upholstery fabrics, car seats, wall coverings, carpeting, blankets, lampshades, plush toys and stuffed animals, towels, and/or the like. Further typical textiles are geotextiles, tents, inner soles of shoes, garments/clothing, such as hats, gloves, socks, trousers, shirts, and the like. However, it will be understood that the formulations of the present disclosure may be applied to textiles and/or surfaces other than those explicitly disclosed herein, including porous, semi-porous, nonporous, and/or non-woven surfaces.

Referring now to FIG. 1, a flowchart of an exemplary method 100 of controlling a lice infestation, such as a human lice infestation, is shown. As discussed above, in one embodiment, the method 100 generally includes applying an anti-lice formulation including an effective amount at least one spinosyn to a textile or surface that is in need of treatment. For example, the textile or surface that is in need of treatment may have a human lice infestation, or may be believed to have a human lice infestation. In one embodiment, the anti-lice formulation includes an effective amount of spinosad. Further, in one embodiment the anti-lice formulation is a ready-to-use anti-lice formulation. For example, the ready-to-use anti-lice formulation may be commercially available to the user as a pre-mixed diluted suspension (for example, an aqueous suspension), diluted solution (for example, an aqueous solution), or mixture thereof having the active ingredient (spinosyn or spinosad) present in a concentration of approximately 1000 ppm (for example, 1000 ppm±200 ppm). As discussed below with respect to exemplary formulations studies, the anti-lice formulations of the present disclosure are effective in controlling a human lice infestation, including eggs, larvae, and adult lice, when applied to a textile or surface. This is in contrast to currently known methods of applying formulations directly to a human or animal subject having a lice infestation and methods of treating a textile or surface having a human lice infestation by heat treatment, vacuum treatment, and/or other methods that do not include applying an anti-lice formulation including at least one spinosyn to the textile or surface.

Continuing to refer to FIG. 1, in a first and only step 102 of the method 100, an anti-lice formulation is applied to a textile or other surface in need of treatment. In one embodiment, the anti-lice formulation is a ready-to-use anti-lice formulation that includes an active amount of a spinosyn, such as 1000 ppm (or 0.1% by weight) spinosad. However, it will be understood that other effective amounts of spinosyn may be used, such as between approximately 50 ppm (or 0.005% by weight) and approximately 5000 ppm (or 0.5% by weight) spinosad (±10 ppm or 0.001% by weight), including between approximately 250 ppm (or 0.025% by weight) and approximately 1000 ppm (or 0.1% by weight) spinosad. In one embodiment, the anti-lice formulation includes an amount of spinosyn that is diluted or mixed with one or more carriers such that the anti-lice formulation is a ready-to-use anti-lice formulation that includes, for example, approximately 1000 ppm (or 0.1% by weight) spinosad.

In one embodiment, the anti-lice formulation is applied to the textile in one step, such as when the anti-lice formulation is a liquid, gel, paste, lotion, foam, spray, or the like. For example, a user may apply the anti-lice formulation to the textile using one or more spray bottles, droppers, dabbing sponges, rollers, or the like, or may be poured over the textile and/or applied with the user's fingers from a suitable vessel. In some embodiments, such as when the anti-lice formulation is a ready-to-use diluted aqueous suspension, the user may shake or agitate the vessel in an optional step to re-suspend any solid particles that may have sedimented out of suspension. In one embodiment, a sufficient amount of the anti-lice formulation is applied to the textile. The amount that is a sufficient amount may depend on the form of the anti-lice formulation, the carrier(s) used, the type of textile, and/or other factors. In one embodiment, an entirety of a predetermined area of the textile (for example, a human-contacting surface of a headrest or pillow) is coated or saturated with the anti-lice formulation, or is otherwise exposed to an amount of the anti-lice formulation. In some embodiments, the anti-lice formulation is allowed to remain on the textile after application and is not washed, rinsed, or otherwise removed from the textile. As is discussed in greater detail below, the anti-lice formulation is formulated such that its remaining on the textile will not adversely affect the textile's integrity or alter the textile's color. Thus, the anti-lice formulation can be used on upholstery, leather, and/or other textiles or surfaces that cannot be conveniently washed or that cannot be washed at all (for example, airplane or car seats, couch upholstery, or the like). However, in some embodiments, the anti-lice formulation may be washed, rinsed, or otherwise removed from the textile. For example, the anti-lice formulation may be applied to and allowed to dry on the textile before the anti-lice formulation is removed. In one non-limiting example, the anti-lice formulation is allowed to dry on the textile for between approximately two and four hours before removal. Further, in some embodiments and as discussed below, the anti-lice formulation has 100% ovicidal activity when applied to a textile in need of treatment and allowed to remain on the textile without being washed or rinsed away.

Figure 2:
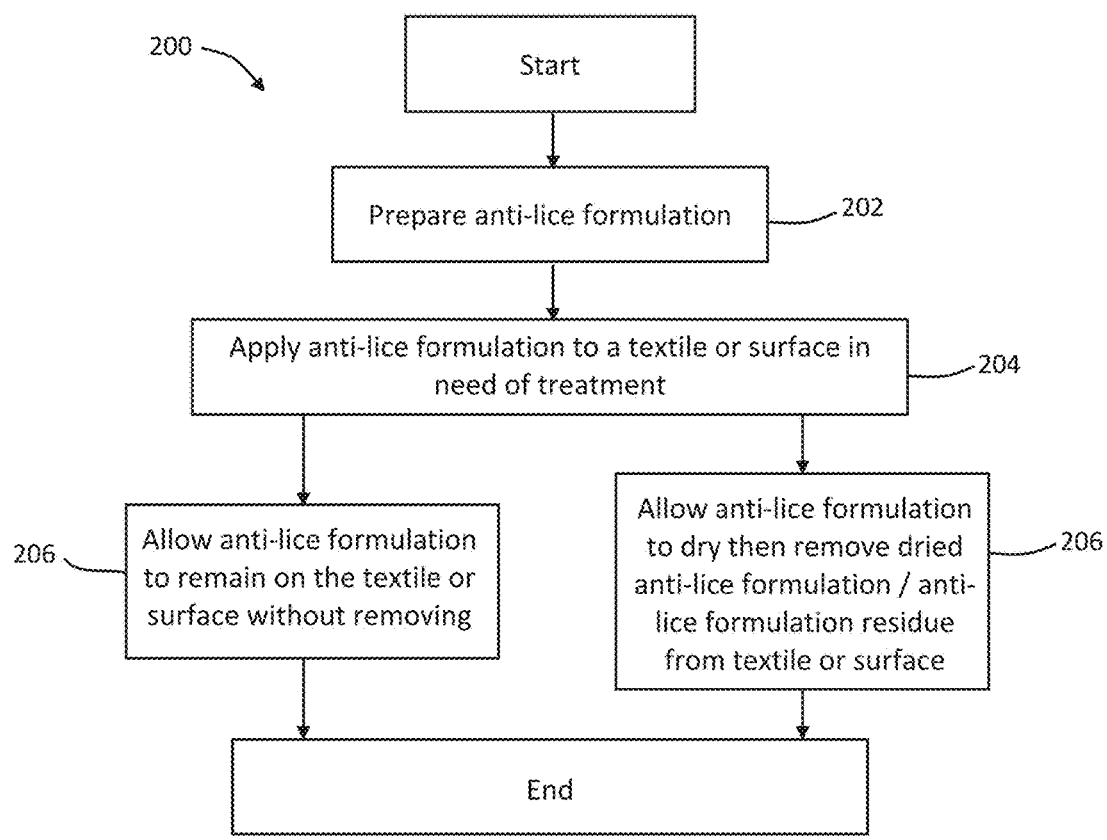
FIG. 2 is a flowchart of another exemplary method of controlling lice, such as human lice in accordance with the present disclosure.

Referring now to FIG. 2, a flowchart of another exemplary method 200 of controlling a lice infestation, such as a human lice infestation, is shown. In one embodiment, the anti-lice formulation includes an active amount of a spinosyn, such as 1000 ppm (or 0.1% by weight) spinosad. However, it will be understood that other effective amounts of spinosyn may be used, such as between approximately 50 ppm (or 0.005% by weight) and approximately 5000 ppm (or 0.5% by weight) spinosad (±10 ppm or 0.001% by weight), including between approximately 250 ppm (or 0.025% by weight) and approximately 1000 ppm (or 0.1% by weight) spinosad.

In a first step 202 of the method 200, an anti-lice formulation is prepared before applying it to the textile. In one embodiment, the anti-lice formulation is prepared by mixing a wettable powder containing an effective amount of spinosyn with a physiologically acceptable carrier and placing the anti-lice formulation into a suitable application vessel, such as a spray bottle, jar, bowl, or the like. In another embodiment, the anti-lice formulation is prepared by mixing a concentrate formulation with water or other carrier to create an aqueous suspension and/or aqueous solution of an effective amount of spinosyn and placing the anti-lice formulation into a suitable application vessel. In one embodiment, the concentrate formulation is a fluid, foam, or gel that is diluted to create a diluted aqueous suspension and/or diluted aqueous solution having the active ingredient (such as spinosyn or spinosad) present in an amount of approximately 1000 ppm (±200 ppm). In another embodiment, the concentrate formulation is a wettable powder that the user then mixes into or adds to water or other carrier in an application vessel or other container to create a diluted aqueous suspension and/or diluted aqueous solution having the active ingredient (such as spinosyn or spinosad) present in an amount of approximately 1000 ppm (±200 ppm). For example, the concentrate formulation and/or wettable powder may be sold in a bottle, jar, in individual pre-measured dosage vials, single-use quick-dissolve packets or sachets, or in other suitable containers or packaging devices.

In a second step 204 of the method 200, the anti-lice formulation is applied to the textile from the application vessel as discussed above regarding FIG. 1. Optionally, the user determines whether a sufficient amount of the anti-lice formulation has been applied to the textile or surface. In one non-limiting example, a sufficient amount of anti-lice formulation is a light mist that entirely covers a desired surface area or area of treatment. In another non-limiting example, a sufficient amount of anti-lice formulation is the amount required to completely saturate a textile or surface. If the user determines that a sufficient amount of the anti-lice formulation has not been applied to the textile, the user then makes one or more additional applications (that is, applies at least one additional amount of the anti-lice formulation to the textile).

Continuing to refer to FIG. 2, in one embodiment the textile is allowed to dry before use thereof and/or before human contact with the textile. In some embodiments, in a third step 206 the user allows the anti-lice formulation to remain on the textile after application and is not washed, rinsed, or otherwise removed from the textile. As is discussed in greater detail below, the anti-lice formulation is formulated such that its remaining on the textile will not adversely affect the textile's integrity or alter the textile's color. Further, in some embodiments and as discussed below, the anti-lice formulation has 100% ovicidal activity when applied to a textile in need of treatment and allowed to remain on the textile without being washed or rinsed away. Thus, the anti-lice formulation can be used on upholstery, leather, and/or other textiles or surfaces that cannot be conveniently washed or that cannot be washed at all. Alternatively, as shown in FIG. 2, the user first allows the anti-lice formulation to dry on the textile and then the user washes, rinses, or otherwise removes the dried anti-lice formulation and/or anti-lice formulation residue from the textile. In one non-limiting example, the anti-lice formulation may dry on the textile within two to four hours, or at least for a period of time that is expected to produce approximately 100% mortality in lice eggs, immatures, and adults, according to the particular anti-lice formulation being used (for example, spinosyn concentration, carrier(s) used, etc.). However, it will be understood that the actual drying time may depend on carrier(s) used in the anti-lice formulation, the textile type, the surrounding environment, etc. In one non-limiting example, the user may remove the dried anti-lice formulation and/or anti-lice formulation residue from the textile by washing the textile in a washing machine, wiping the textile with a damp cloth, hosing the textile with water, or the like.

Referring now to FIG. 3, a flowchart of an exemplary method 300 of preparing an anti-lice formulation is shown. In one embodiment, the method 300 generally includes the step 302 of adding an amount of spinosyn (such as spinosad) to a carrier to produce at least one of a suspension and a solution in which the spinosyn is present in a concentration of approximately 1000 ppm (for example, 1000 ppm±200 ppm). In one embodiment, the anti-lice formulation is at least one of an aqueous suspension and an aqueous solution. Thus, in one embodiment, the method 300 is a method of preparing a ready-to-use anti-lice formulation that will not affect the integrity of a textile or surface to which it is applied, even if the anti-lice formulation is not washed, rinsed, or otherwise removed from the textile or surface.

Continuing to refer to FIG. 3, the spinosyn that is added to the carrier is a concentrate formulation in which spinosyn is present in a concentration of from approximately 2.5% to approximately 44.2% by weight of active ingredient. In some embodiments, the concentrate formulation is from approximately 0.5% to approximately 45%, including 44.2%, by weight of active ingredient. In one embodiment, the concentrate formulation is then diluted to create a ready-to-use anti-lice formulation, such as a diluted aqueous suspension and/or diluted aqueous solution. For example, in one embodiment an amount of spinosyn is added to an amount of non-organic carrier sufficient to dilute the spinosyn to create an anti-lice formulation in which the spinosyn is present in a concentration of approximately 1000 ppm. In one embodiment, the concentrate formulation is diluted with water or other non-organic carrier fluid until the active spinosyn is present in the resulting ready-to-use anti-lice formulation in a concentration of approximately 1000 ppm (for example, 1000 ppm±200 ppm). Although FIG. 3 shows a method of producing an anti-lice formulation in which the spinosyn is present in a concentration of approximately 1000 ppm, it will be understood that the spinosyn may be present in a concentration of about 1 ppm (or 0.0001% by weight) to about 10,000 ppm (or 1% by weight), from about 50 ppm (or 0.005% by weight) to about 5,000 ppm (or 0.05% by weight), from about 100 ppm (or 0.01% by weight) to about 2500 ppm (or 0.25% by weight), and from about 250 ppm (or 0.25% by weight) to about 1000 ppm (or 0.1% by weight).

Continuing to refer to FIG. 3 and as noted above, the non-organic carrier may include any suitable fluid ingredient, or combinations thereof, in which spinosyn is at least partially soluble and/or appropriately suspended, but that is not reasonably expected to affect (for example, adversely affect) the textile's integrity and/or colorfastness. In some embodiments, the carrier is water. Thus, the anti-lice formulation preferably does not include carriers such as oils or "harsh" organic solvents such as dimethyl sulfoxide (DMSO), N-methyl-2-pyrrolidone (NMP), petroleum distillates, acetates, ketones, or the like, even if the spinosyn were at least partially soluble and/or appropriately suspended in such carriers, as carriers of this type would be expected to affect the integrity of a textile. Likewise, in some embodiments, the anti-lice formulation does not include additives or other secondary ingredients of a similar type (that is, "harsh" organic solvents), or at least does not include such additives or other secondary ingredients in a concentration or amount that would reasonably be expected to affect the textile's integrity. Conversely, in one embodiment the anti-lice formulation may include one or more carriers or additives or other secondary ingredients that are "weak" organic solvents or solubilizing agents that are at least partially miscible in water and that are not (or are not included in concentrations that are) reasonably expected to affect the textile's integrity. These "weak" organic solvents may include but are not limited to propylene glycol, small-chain aromatic or aliphatic alcohols, surfactants, or the like. For example, such "weak" organic solvents may be added to the anti-lice formulation (or may be included in the concentrate formulation and some amount may remain in the anti-lice formulation when the concentrate formulation is diluted) to enhance or improve certain qualities of the anti-lice formulation such as the solubility of spinosyn, suspension of spinosyn, temperature stability, spray properties, wetting properties, or the like. Thus, in some embodiments the anti-lice formulation is referred to as having a non-organic carrier as a primary ingredient, even if some small amounts of organic additives are present, as long as the organic additives are not reasonably expected to affect the textile's integrity.

Continuing to refer to FIG. 3, in an optional second step (not shown), the resulting anti-lice formulation is bottled or otherwise packaged for consumer use. Non-limiting examples include spray bottles, bottles, jugs, vials, packets, or the like.

Referring now to FIGS. 4-13, various studies testing the efficacy of one or more anti-lice formulations and the suitability of one or more anti-lice formulations are discussed.

Study 1

Referring now to FIGS. 4 and 5, results of an exemplary first study (Study 1) analyzing the impacts of an anti-lice formulation on lice viability at all life stages are shown. FIG. 4 shows the impact of the anti-lice formulation on lice egg viability and FIG. 5 shows the impact of the anti-lice formulation on adult and immature lice viability. In one non-limiting method of analyzing viability results, the protocol as set forth in Yoon et al., AN IMPROVED IN VITRO REARING SYSTEM FOR THE HUMAN HEAD LOUSE ALLOWS THE DETERMINATION OF RESISTANCE TO FORMULATED PEDICULICIDES, Pesticide Biochemistry and Physiology, 86 (2006) pp. 195-202, is substantially followed. The results of Study 1 show that the application of an anti-lice formulations including spinosad in any of a variety of concentrations decreased hatchability over the negative control and increased mortality in both adults and immature lice over the negative control.

In this exemplary study, permethrin-resistant human head lice (*Pediculus humanus capitis*, BR-HL strain), originally collected from infested children in Bristol, UK, and maintained on an in vitro rearing system at the University of Massachusetts at Amherst, was used for all mortality and ovicidal assays. Young (1-2 days post emersion) adult lice (15 females+15 males, N=30) were placed onto an individual human hair tuft in a Petri dish. Immature lice (10 first, 10 second, and 10 third instars, N=30) were placed onto an individual hair tuft in a Petri dish. Eggs (approximately 30 eggs/hair tuft, at mixed developmental stages) were oviposited on tufts in a Petri dish over a period of 1-2 days and the adults (5 mating pairs) were removed. All tufts infested with lice/eggs as described above were treated with various anti-lice formulations or distilled deionized $H_2O$ (dd$H_2O$, water-treated negative control). That is, each tuft infested with lice/eggs was treated with one of a first anti-lice formulation having a 1000 ppm concentration of spinosad, a second anti-lice formulation having a 500 ppm concentration of spinosad, a third anti-lice formulation having a 250 ppm concentration of spinosad, and deionized $H_2O$ (dd$H_2O$, water-treated negative control). In one embodiment, a concentrate formulation having 0.5% spinosad) and then diluted with water to achieve the desired spinosad concentrations is used.

At the end of the 10-minute exposure period, the spinosad-treated and dd$H_2O$-treated tufts were dried on filter paper for 5 minutes at room temperature. Hair tufts were gently stirred in the formulated product until all hairs were covered by visual inspection (approximately 6-8 circular motions). The anti-lice formulation was then rinsed out of each hair tuft by three serial washings in distilled, deionized water (50 ml per hair tuft) for 2 minutes (40 seconds per wash). Treated hair tufts were gently swirled in water during washing using blunt forceps. Excess water was removed from the hair tufts by placing them on filter paper and allowing them to air-dry for 20-30 minutes. Dried hair tufts were transferred to the in vitro rearing system and percent mortality of each treatment was determined on the eighth day post treatment. Identical second treatments were applied to tufts in which surviving lice were found, following the above procedures and cumulative percent mortality was determined on the fifteenth day following the application of the first treatments.

Dried tufts with adults or immature lice were placed into blood feeding cups and maintained on the in vitro rearing system. Tufts with eggs were placed into covered sterile glass Petri dishes and moved to an incubator at 31° C., 70-80% relative humidity (RH).

Mortality of adult and immature lice was assessed at 60 and 120 minutes following exposure and then at 12, 24, and 48 hours, or until 100% mortality was seen under a stereomicroscope. Death was determined by absence of appendage movement when the lice were probed. Egg viability was recorded daily by examining individual eggs for proper size, shape, and color to determine survivorship of eggs throughout their development before and after treatment (7-13 days). The number of lice that hatched from eggs was recorded and used to determine the percent hatchability of eggs. Undeveloped eggs and stillborn lice were determined to be, and were recorded as, dead. Hatchability of eggs was calculated using the following equation (1):

$$\% \text{ hatchability} = H/N \times 100 \qquad (1)$$

where H is the number of eggs hatched and N is the total number of eggs oviposited. The above procedure is a proven standard for assessing compounds and formulations intended for ultimate use on human scalp.

Anti-lice formulations having various concentrations of spinosad were used, as well as the negative control (dd$H_2$0), and the results are set forth in FIGS. 4 and 5. As can be seen in FIGS. 4 and 5, the application of spinosad decreased hatchability over the negative control and increased mortality in both adults and immature lice over the negative control.

Study 2

Referring now to FIGS. 6-8, results of an exemplary second study (Study 2) analyzing the impacts of an anti-lice formulations on lice viability at all life stages are shown. FIG. 6 is a chart showing exemplary treatment formulations and exposure times, FIG. 7 shows the impact of the anti-lice formulations on lice egg viability, and FIG. 8 shows the impact of the anti-lice formulations on adult and immature lice viability. In this exemplary study, the protocols as set forth in Yoon et al. and in Study 1, above, were generally employed. Some deviations to the published method were used to better reflect the intended use of spraying a textile and delaying any further washing or leaving the sprayed material intact, as the published method is designed to best fit situations in which treatment is followed by rinsing or washing the anti-lice formulation from the tufts completely. That is, the methods were adapted to a desired method of using the anti-lice formulations in which the anti-lice formulations are applied to a textile and not rinsed or washed from the textile. Thus, instead of using a treatment or water bath to swirl tufts into the diluted treatments, a hand pumped spraying method was used instead. Also, rather than rinsing three times in water after initial application and treatment to look for residual effects, no rinsing was used in Study 2 to best reflect the intended use pattern. The results of Study 2 indicate that application of an anti-lice formulation having 1000 ppm spinosad may produce 100% ovicidal activity (0% hatchability) of eggs, as well as 100% mortality of immature and adult lice, which is greater than results produced by application of both the negative control and the positive control used in the study.

Efficacy of an anti-lice formulation having 1000 ppm spinosad (for example, a concentrate formulation having spinosad at 0.5% and then diluted with water to achieve 1000 ppm spinosad) was examined following treatment via spraying of human head louse adults, mixed stages of larval instars, and oviposited eggs, using both positive and negative controls. All tufts infested with lice/eggs as described above were treated with either a 1000 ppm solution of spinosad, distilled deionized $H_2O$ (dd$H_2O$, water-treated negative control), or a positive control. That is, each tuft infested with lice/eggs was treated with one of an anti-lice formulation having a 1000 ppm concentration of spinosad, distilled deionized $H_2O$ (dd$H_2O$, water-treated negative control), or a positive control. For example, NIX® was used as the positive control.

A lice/egg-infested tuft was saturated by spraying the tuft with the treatment until complete coverage was achieved by visual inspection. To establish consistent applications for each treatment, in one embodiment a hair tuft and spray bottle were clamped into positions using two ring stands. The ring stands were positioned approximately 5 inches apart at their bases. The flattened hair tuft was placed perpendicular to the direction of the spray bottle, angled down at 45 degrees to the spray bottle, and placed 4 inches from the applicator tip. Six pumps of the bottle were applied to one side of the tuft, then the tuft was turned 180 degrees and six more pumps were applied to the other side for a total of 12 pumps.

For a positive control treatment, a water-dampened tuft with lice/eggs was saturated by immersion into 0.5 ml of NIX® in a small glass beaker. For a negative control, a dry tuft with lice/eggs was saturated by spraying it with 12 pumps of $ddH_2O$. The NIX®-treated and $ddH_2O$-treated tufts were individually transferred to a new Petri dish and stored in an incubator (31° C., 70-80% RH) for exposure time intervals as indicated in FIG. 6 (namely, 10 minutes).

At the end of the 10-minute exposure period, the spinosad-treated and $ddH_2O$-treated tufts were dried on filter paper for 5 minutes at room temperature. The NIX®-treated tufts were treated with 0.5 ml of a soap or shampoo, such as JOHNSON'S® (Johnson & Johnson, Brunswick, N.J.) baby shampoo at the end of the exposure period and sequentially washed in three separate $ddH_2O$ baths (300 ml/bath) for 40 seconds per wash and then dried on filter paper for 5 minutes at room temperature.

Dried tufts with adults or immature lice were placed into blood feeding cups and maintained on the in vitro rearing system. Tufts with eggs were placed into covered sterile glass Petri dishes and moved to an incubator at 31° C., 70-80% RH.

Mortality of adult and immature lice were assessed at 60 and 120 minutes following exposure and then at 12, 24, and 48 hours or until 100% mortality was seen under a stereomicroscope. Death was determined by absence of appendage movement when probed. Egg viability was recorded daily by examining individual eggs for proper size, shape, and color to determine survivorship of eggs throughout their development before and after treatment (7-10 days). The number of lice that hatch from eggs was recorded and used to determine the percent hatchability of eggs. Undeveloped eggs and stillborn lice were recorded as dead. Hatchability of eggs was calculated using Equation (1) above, namely:

$$\% \text{ hatchability} = H/N \times 100 \qquad (1)$$

where H is the number of eggs hatched and N is the total number of eggs oviposited.

Where possible, log time versus logit mortality/% hatchability regressions were generated to determine $LT_{50}$ values and maximum log-likelihood ratio tests performed to test equality (slope and intercept) of the regression lines (for example, using POLO PC™, LeOra Software). Due to the speed of the killing action of the spinosad in the formulation on lice, this analysis was not always possible.

FIG. 7 shows results of the ovicidal action of the anti-lice formulation having 1000 ppm spinosad compared with the negative control (water only) and the positive control (NIX® formulation, 1% permethrin). None of the eggs treated with the anti-lice formulation having 1000 ppm spinosad (n=30) hatched, resulting in 0% hatchability. The water-treated eggs (n=49) all hatched between days 7-11 post-treatment, resulting in 100% hatchability. The NIX®-treated eggs (n=60) had an overall hatchability of 52% with hatching beginning at 9 days post treatment and continuing till 11 days.

FIG. 8 shows the mortality response for adults (15 females and 15 males, n=30) over 11 days post treatment. Adults treated with the anti-lice formulation having 1000 ppm spinosad formulation all died (30/30, 100% mortality) within 24 hours of treatment, with mortality beginning after 2 hours post treatment. The water-treated adults (n=30) began dying at 6 days post treatment, resulting in 20% mortality at 11 days post treatment (6/30). The NIX®-treated adults began dying at 3 days post treatment, resulting in 67% mortality (20/30) at 11 days post treatment.

Immature lice (10 first, 10 second and 10 third instars, n=30) all died within the first 24 hours post treatment with the anti-lice formulation having 1000 ppm spinosad (100% mortality), with mortality beginning at 2 hours post treatment. Water-treated immature lice began dying at 5 days post treatment and resulted in 7% mortality (2/30) over the 11-day experiment. NIX®-treated immature lice began dying at 1 day post treatment, and continued to die over the next 3 days, resulting in 90% mortality (27/30).

The anti-lice formulation having 1000 ppm spinosad applied as a spray to egg/lice-infested human hair tufts resulted in 0% egg hatch (100% ovicidal activity) and 100% mortality of both adult and immature lice. Thus, this 1000-ppm spinosad anti-lice formulation is fast-acting on both adult and immature lice, killing all the lice within 24 hours post application. The water-treated adults and immature lice experienced mortality that ranged from 7-20% and the water-treated eggs suffered no mortality. The NIX®-treated adults and immature lice experienced mortality that ranged from 67% for adults to 90% for immature lice. Thus, the 1000-ppm spinosad anti-lice formulation applied as a spray is an effective ovicidal for the treatment of textiles.

Study 3

Figure 11:
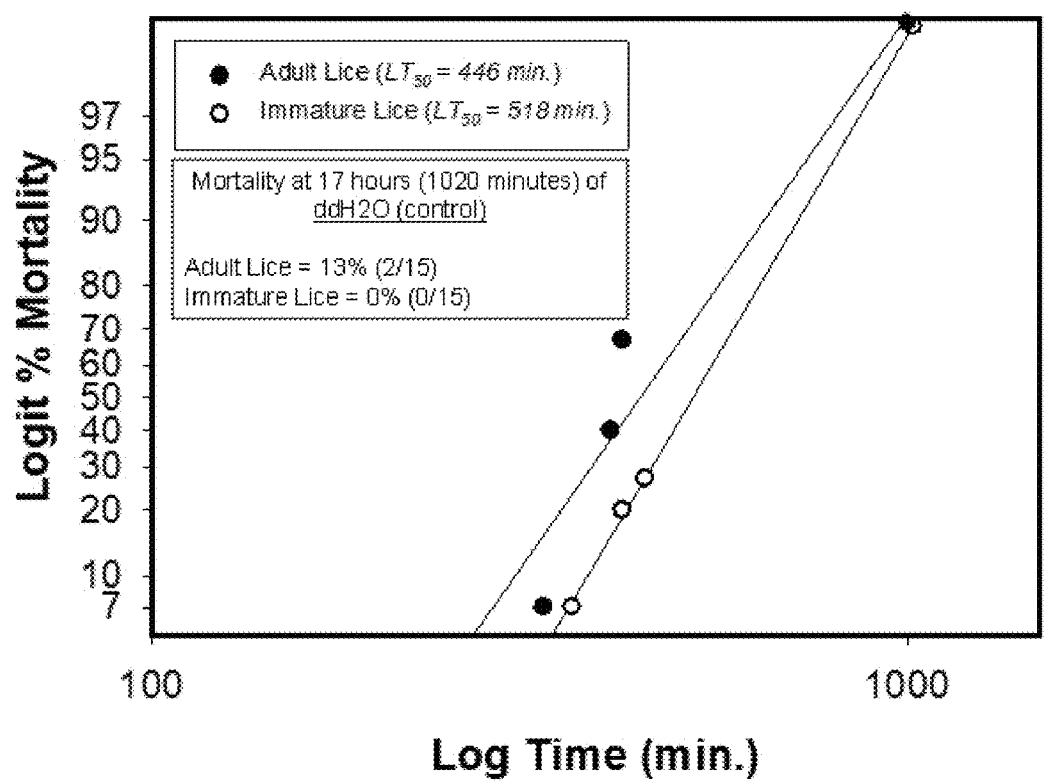
FIG. 11 is a graph showing a logit % mortality of adult lice and immature lice plotted against time when treated with an anti-lice formulation according to the present disclosure in the exemplary third study.
Figure 13:
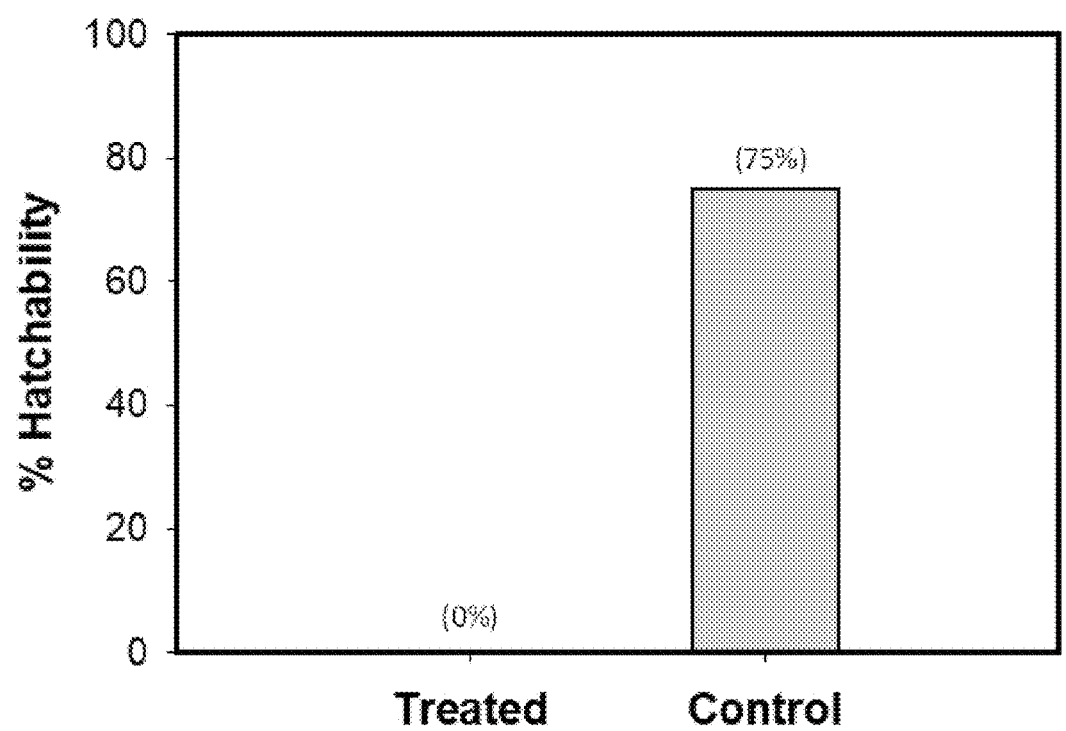
FIG. 13 is a graph showing hatchability of eggs following spray application of both an anti-lice formulation according to the present disclosure (treated) and deionized water (negative control) to a fabric in the exemplary third study.

Referring now to FIGS. 9-13, results of an exemplary third study (Study 3) to determine the efficacy of an anti-lice formulation having 1000 ppm spinosad (for example, a concentrate formulation having spinosad at 0.5% and then diluted with water to achieve the desired spinosad concentration) versus a negative control on human head louse adults, mixed larval stages, and oviposited eggs following spray treatment onto fabric are shown. The impact of the anti-lice formulation on adult and immature lice viability is shown in absolute numbers, where values represent the number of dead lice at given time points (not cumulative), in FIG. 9 and in percentages, where values represent cumulative percentage of dead lice at given time points, in FIG. 10. FIG. 11 is a graph showing a logit % mortality of adult lice and immature lice plotted against time; FIG. 12 is a chart showing hatchability of eggs following spray application of both an anti-lice formulation (treated) and distilled deionized water ($ddH_2O$) (control) to a textile; and FIG. 13 is a graph showing hatchability of eggs following spray application of both an anti-lice formulation (treated) and distilled deionized water ($ddH_2O$) (control) to a textile. The results of Study 3 indicate that application of an anti-lice formulation having 1000 ppm spinosad to a textile produces 100% ovicidal, nymphicidal, and adulticidal activity.

In the exemplary third study (Study 3), permethrin- and malathion-resistant human head lice (*Pediculus humanus capitis*, BR-HL strain), which were originally collected from infested children in Bristol, UK, and maintained on an in vitro rearing system at the University of Massachusetts at Amherst [1], were used for all mortality and ovicidal assays.

Young (1-2 days post emersion) adult lice (15 mixed females and males, N=15) were placed onto a single side of a cloth fabric swatch (1"×1" square) along with mixed immature lice (approximately five first instars, approximately five second instars, and approximately five third instars, N=15) for a total of 30 live lice per experiment/fabric swatch. Eggs (approximately 30 eggs/cloth fabric square, at mixed developmental stages) were oviposited onto a single side of an identical fabric swatch over a period of 1-2 days and the adults (5 mating pairs) were removed. All fabric swatches infested with lice/eggs as described above were treated with either an anti-lice formulation having a 1000 ppm concentration of spinosad or with distilled deionized H$_2$O (ddH$_2$O, water-treated negative control) using the hand pumped spraying method. Briefly, a louse/egg-infested fabric swatch was saturated by spraying the treatment onto the fabric swatch until complete coverage was achieved by visual inspection. A non-limiting exemplary optimized spraying technique was used that includes spraying 5 pumps of the treatment to each side of a flattened fabric swatch infested with lice/eggs, which is held in place using a laboratory clamp at a 45 degree angle downward. A treated fabric swatch with lice or eggs was transferred to a new Petri dish and stored in an incubator (31° C., 70-80% RH). Treatment/exposure time was set at 10 minutes for both lice and eggs.

For each treatment, in one embodiment a fabric swatch and spray bottle were clamped into position using two ring stands. The ring stands are positioned approximately 5 inches apart at their bases. The flattened fabric swatch was placed perpendicular to the direction of the spray bottle, angled down at 45 degrees to the spray bottle and placed 4 inches from the applicator tip. Five pumps of the spray applicator were applied to each side of the fabric.

For a negative control, a fabric swatch with lice/eggs as saturated by spraying with ddH$_2$O as described above for treated fabric swatches. Fabric swatches treated with ddH$_2$O were individually transferred to new petri dish and stored in an incubator (31° C., 70-80% RH) as above.

At the end of the 10-minute exposure period, the fabric swatches (both those treated with the 1000 ppm spinosad anti-lice formulation and those treated with the ddH$_2$O) were dried on filter paper for 5 minutes at room temperature.

Dried fabric swatches with adults and immature lice or eggs were placed into covered sterile glass Petri dishes and moved to an incubator at 31° C., 70-80% RH.

Mortality of adult and immature lice was assessed at 15-minute intervals for the first 7.5 hours following exposure and then at every 17 hours until 100% mortality was seen under a stereomicroscope. This procedure was adjusted using the results from a preliminary exposure test to include knockdown, as 100% mortality took between approximately 8-17 hours. Knockdown was determined when a louse was not being able to right itself, but had appendage movements (although movement may be limited and/or delayed). Death was determined by absence of appendage movement when the louse was probed.

Egg viability was recorded daily by examining individual eggs for proper size, shape, and color to determine survivorship of eggs throughout their development before and after treatment (7-10 days or until all ddH$_2$O eggs hatch). The number of lice that hatched from eggs was recorded and used to determine the percent hatchability of eggs. Undeveloped eggs and stillborn lice were recorded as dead. Hatchability of eggs is calculated using Equation (1) above, namely:

$$\% \text{ hatchability} = H/N \times 100 \tag{1}$$

where H is the number of eggs hatched and N is the total number of eggs oviposited.

Where possible, log time versus logit mortality/% hatchability regressions were generated to determine LT$_{50}$ values and maximum log-likelihood ratio tests performed to test equality (slope and intercept) of the regression lines (for example, using POLO PC™, LeOra Software).

FIG. 9 is a chart showing exemplary adult and immature lice mortality following spray application of both the anti-lice formulation (treated) and deionized water (control) on beige fabric. Values represent number of dead lice at given time points (not cumulative). Lice were considered "knockdown" after lack of movement on fabric and limited/delayed appendage movement after probing.

FIG. 10 is a chart showing exemplary adult and immature lice percentage of mortality following spray application of both the anti-lice formulation (treated) and deionized water (control) on beige fabric. Values represent cumulative percentage of dead lice at given time points. Lice were considered "knockdown" after lack of movement on fabric and limited/delayed appendage movement after probing.

FIG. 11 is a graph showing log odds ratio (or "logit") percentage of mortality of adult lice (black data points) and immature lice (white data points) following spray application of the anti-lice formulation on beige fabric. Median lethal time (LT$_{50}$) was presented for both adult and immature lice following treatment with the anti-lice formulation. Mortality of the control group was calculated at the end of the bioassay (17 hours).

FIG. 12 is a chart showing hatchability of eggs following spray application of both the anti-lice formulation (treated) and deionized water (control) on beige fabric. Fabrics were sprayed with 5 pumps on each side until saturation. Values represent number of lice hatched from eggs on days after treatment, with total percentage of hatchability of eggs given at the bottom of the chart.

FIG. 13 is a graph showing hatchability of eggs following spray application of both the anti-lice formulation (treated) and deionized water (control) on beige fabric. Fabrics were sprayed with 5 pumps on each side until saturation. Values represent number of lice hatched from eggs on days after treatment.

Discussions and Conclusions

Adult and immature lice: All treated adult and immature lice were knocked down by 75 minutes post treatment (as shown in FIGS. 9 and 10). No control lice were knocked down by this same time (also as shown in FIGS. 9 and 10). Adult lice treated with the anti-lice formulation first died at 330 minutes, 10 were dead at 420 minutes, and all were dead by 1020 minutes. Immature lice treated with the anti-lice formulation first died at 360 minutes, 5 were dead at 450 minutes, and all were dead at 1020 minutes. No control adult lice were knocked down and only 2 of 15 (13%) died at 1020 minutes on fabric swatches treated with ddH$_2$O. No control immature lice were knocked down and none died at 1020 minutes on fabric squares treated with ddH$_2$O.

The adult lice have a treatment LT$_{50}$ value of 0.86 of treatment LT$_{50}$ value of the immature lice (as shown in FIG. 11), so the adult lice may be slightly more sensitive. However, without replications, a statistical treatment is not performed. The difference between them, however, appears small.

Ovicidal Activity: No eggs hatched (FIGS. 11 and 12) on fabric swatches treated with the anti-lice formulation (0% hatchability). Ten of 40 untreated eggs (ddH2O controls) hatched (75% hatchability).

Summary: Under the experimental conditions used, the efficacy of an anti-lice formulation having 1000 ppm of spinosad applied to fabric was 100% adulticidal, nymphicidal, and ovicidal to the BR-HL strain of human head lice.

Study 4

An exemplary fourth study (Study 4) was performed to evaluate the colorfastness and integrity of commonly used textiles following exposure to an anti-lice formulation having a concentration of 1000 ppm spinosad (i.e., the same anti-lice formulation used in Study 3). The results of Study 4 show that application of an anti-lice formulation having 1000 ppm spinosad to a textile does not affect the textile's integrity or color.

In the exemplary fourth study (Study 4), an anti-lice formulation having 5000 ppm spinosad (for example, a concentrate formulation having spinosad at 0.5%) was used. The concentration of spinosad was then reduced from 5000 ppm to 1000 ppm with water and mixed by agitation to ensure a homogeneous suspension immediately prior to application to fabric swatches.

In the exemplary fourth study, fabric swatches measuring approximately 6 inches square were used. The fabric samples included cotton, polyester, nylon, and olefin in a variety of finishes including percale, linen, fleece and woven upholstery. Further, the fabric swatches included different colors representing a range of dyes commonly used in commercial fabrics.

The fabric swatches were placed onto a water-absorbent barrier in a grid pattern. Swatches were adequately separated to ensure no exposure to the active ingredient from adjacent swatches occurred during application. A ridged barrier was held vertically against the midline of each fabric sample to limit the area of exposure to the active ingredient to one half of each fabric swatch, which enabled each sample to serve as its own untreated control (that is, each fabric swatch as divided into a treated portion and an untreated portion). The right lower corner of each sample was clipped or otherwise marked to indicate the treated side of the sample.

The anti-lice formulation (approximately 2.5 ml, two sprays) was sprayed onto half of each fabric swatch using a single spray bottle to ensure even saturation of the treated portion of each of the fabric swatches. The fabric swatches were then left in place to allow the anti-lice formulation (and, therefore, the active ingredient) to dry on the fabric for approximately two hours. The dried fabric swatches were then washed (such as in a residential front load washing machine) using cold water on the gentle cycle using a detergent such as TIDE® (Procter & Gamble Company, Cincinnati, Ohio) liquid detergent. Samples were allowed to air dry after washing.

Both the untreated and treated halves of each fabric swatch were observed visually under LED illumination prior to exposure to the anti-lice formulation, after the swatches were dry and prior to washing, and again after the samples were dry following washing. Digital photographs of each fabric swatch were obtained at each observation period to document fabric integrity and colorfastness. The SDHC flash memory card used to capture the files in the camera was considered the source data for this study.

Visual observations comparing the untreated side to the treated side of each fabric swatch did not reveal any observable changes in either fabric integrity (for example, no fraying, tearing, ripping, or other damage occurred and/or was observed) or the colorfastness for these swatches following initial exposure to the anti-lice formulation (i.e. an anti-lice formulation a concentration of spinosad at 1000 ppm) or following drying of the product on the fabric sample. Further, the visual appearance of fabric swatches following washing and drying indicated some fraying of the fabric along the edges and increased wrinkling of the samples, but these observations were similar for both the untreated side and the treated side of each fabric swatch. These observations suggested the changes in fabric integrity were likely associated with the laundering of the samples instead of the treatment with the anti-lice formulation. Still further, visual observations comparing the untreated side to the treated side of each fabric swatch did not reveal any observable changes in colorfastness for these samples following exposure to the anti-lice formulation after washing and air drying of the samples.

Based upon these observations, it is reasonable to conclude that exposure to an anti-lice formulation in accordance with the present disclosure (for example, an anti-lice formulation including spinosad, such as an anti-lice formulation having a concentration of 1000 ppm spinosad) has no impact upon colorfastness and/or fabric integrity for the fabric type, finish and color combinations evaluated. The samples used in this study represent some of the most commonly used types of fibers and finishes used in the commercial textile industry.

Although some studies (for example, Study 3 and Study 4) included the use of an anti-lice formulation having a 1000 ppm concentration of spinosad, it will be understood that the formulations and methods discussed herein could also include other concentrations of spinosyn (for example, spinosad), such as concentrations of between approximately 50 ppm to about 5000 ppm spinosyn.

Embodiments

In one embodiment, a method of controlling human lice infestation comprises applying an ectoparasiticidal amount of a spinosyn in a formulation to a textile in need thereof. In one aspect of the embodiment, said spinosyn is spinosad or a physiologically acceptable salt thereof. In one aspect of the embodiment, said spinosyn is spinosad. In one aspect of the embodiment, the application is carried out with one or more additional active ingredients. In one aspect of the embodiment, the application is carried out with one or more additional active ingredients, said one or more active ingredients are selected from the group of other spinosyns, synthetic pyrethroids, natural pyrethins, organophosphates, organochlorines, carbamates, foramidines, avermectins, milbemycins, isoxazoles, insect growth regulators (including chitin synthesis inhibitors, juvenile hormone analogs, and juvenile hormones), nitromethylenes, pyridines and pyrazoles. In one aspect of the embodiment, said application is carried out using a liquid formulation. In one aspect of the embodiment, said application is carried out using a liquid formulation where said liquid formulation is at least one of an aqueous suspension and aqueous solution. In one aspect of the embodiment, said spinosyn is present in the formulation in an amount from about 50 to about 5000 ppm. In one aspect of the embodiment, said spinosyn is present in the formulation in an amount from about 250 to about 1000 ppm. In one aspect of the embodiment, said human lice is *Pediculus humanus capitis*. In one aspect of the embodiment, said human lice is *Pediculus humanus humanus*. In one aspect of the embodiment, said human lice is *Pthirus pubis*. In one aspect of the embodiment, said textile is selected from bedding, upholstered furniture or clothing.

In one embodiment, a formulation for controlling human lice infestations by application to a textile in need thereof comprises an ectoparasiticidal amount of a spinosyn and a suitable carrier. In one aspect of the embodiment, said spinosyn is spinosad or a physiologically acceptable salt thereof. In one aspect of the embodiment, said spinosyn is spinosad. In one aspect of the embodiment, the application is carried out with one or more additional active ingredients. In one aspect of the embodiment, the application is carried out with one or more additional active ingredients, said one or more active ingredients are selected from the group of other spinosyns, synthetic pyrethroids, natural pyrethins, organophosphates, organochlorines, carbamates, foramidines, avermectins, milbemycins, isoxazoles, insect growth regulators (including chitin synthesis inhibitors, juvenile hormone analogs, and juvenile hormones), nitromethylenes, pyridines and pyrazoles. In one aspect of the embodiment, said application is carried out using a liquid formulation. In one aspect of the embodiment, said application is carried out using a liquid formulation where said liquid formulation is at least one of an aqueous suspension and aqueous solution. In one aspect of the embodiment, said spinosyn is present in the formulation in an amount from about 50 to about 5000 ppm. In one aspect of the embodiment, said spinosyn is present in the formulation in an amount from about 250 to about 1000 ppm. In one aspect of the embodiment, said human lice is *Pediculus humanus capitis*. In one aspect of the embodiment, said human lice is *Pediculus humanus humanus*. In one aspect of the embodiment, said human lice is *Pthirus pubis*. In one aspect of the embodiment, said textile is selected from bedding, upholstered furniture or clothing.

One embodiment includes a spinosyn for use in controlling human lice infestation through application of an ectoparasiticidal amount of said spinosyn in a formulation to a textile in need thereof. In one aspect of the embodiment, said spinosyn is spinosad or a physiologically acceptable salt thereof. In one aspect of the embodiment, the application is carried out with one or more additional active ingredients. In one aspect of the embodiment, the application is carried out with one or more additional active ingredients, said one or more active ingredients are selected from the group of other spinosyns, synthetic pyrethroids, natural pyrethins, organophosphates, organochlorines, carbamates, foramidines, avermectins, milbemycins, isoxazoles, insect growth regulators (including chitin synthesis inhibitors, juvenile hormone analogs, and juvenile hormones), nitromethylenes, pyridines and pyrazoles. In one aspect of the embodiment, said application is carried out using a liquid formulation. In one aspect of the embodiment, said application is carried out using a liquid formulation where said liquid formulation is at least one of an aqueous suspension and an aqueous solution. In one aspect of the embodiment, said spinosyn is present in the formulation in an amount from about 50 to about 5000 ppm. In one aspect of the embodiment, said spinosyn is present in the formulation in an amount from about 250 to about 1000 ppm. In one aspect of the embodiment, said human lice is *Pediculus humanus capitis*. In one aspect of the embodiment, said human lice is *Pediculus humanus humanus*. In one aspect of the embodiment, said human lice is *Pthirus pubis*. In one aspect of the embodiment, said textile is selected from bedding, upholstered furniture or clothing.

One embodiment includes the use of a spinosyn in controlling human lice infestation through application of an ectoparasiticidal amount of spinosad in a formulation to a textile in need thereof. In one aspect of the embodiment, said spinosyn is spinosad or a physiologically acceptable salt thereof. In one aspect of the embodiment, the application is carried out with one or more additional active ingredients. In one aspect of the embodiment, the application is carried out with one or more additional active ingredients, said one or more active ingredients are selected from the group of other spinosyns, synthetic pyrethroids, natural pyrethins, organophosphates, organochlorines, carbamates, foramidines, avermectins, milbemycins, isoxazoles, insect growth regulators (including chitin synthesis inhibitors, juvenile hormone analogs, and juvenile hormones), nitromethylenes, pyridines and pyrazoles. In one aspect of the embodiment, said application is carried out using a liquid formulation. In one aspect of the embodiment, said application is carried out using a liquid formulation where said liquid formulation is at least one of an aqueous suspension and an aqueous solution. In one aspect of the embodiment, said spinosyn is present in the formulation in an amount from about 50 to about 5000 ppm. In one aspect of the embodiment, said spinosyn is present in the formulation in an amount from about 250 to about 1000 ppm. In one aspect of the embodiment, said human lice is *Pediculus humanus capitis*. In one aspect of the embodiment, said human lice is *Pediculus humanus humanus*. In one aspect of the embodiment, said human lice is *Pthirus pubis*. In one aspect of the embodiment, said textile is selected from bedding, upholstered furniture or clothing.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of controlling an infestation of human lice, the method comprising:
    applying an anti-lice formulation to a textile, the anti-lice formulation including an effective amount of an active ingredient and a non-organic carrier, the active ingredient being a spinosyn that is present in the anti-lice formulation in an amount of approximately 1000 ppm, the anti-lice formulation being effective against all life-cycle stages of the human lice and causing 100% mortality in human lice adults, immatures, and eggs when applied to the textile.

2. The method of claim 1, wherein the spinosyn is at least one of a spinosad, a physiologically acceptable salt of a spinosyn, and a physiologically acceptable derivative of a spinosyn.

3. The method of claim 1, wherein the anti-lice formulation further includes at least one additional active ingredient, the at least one additional active ingredient being at least one avermectin.

4. The method of claim 1, wherein the anti-lice formulation is a liquid formulation, the liquid formulation being at least one of an aqueous solution and an aqueous suspension, applying the anti-lice formulation to the textile including spraying the anti-lice formulation onto the textile.

5. The method of claim 1, wherein the anti-lice formulation is a wettable powder, the method further comprising:
    mixing the wettable powder with a liquid non-organic carrier before applying the anti-lice formulation to the textile.

6. The method of claim 1, wherein the anti-lice formulation is prepared from a concentrate formulation, the concentrate formulation including the spinosyn in a concentration of greater than 1000 ppm, the method further comprising:

diluting the concentrate formulation with a non-organic liquid carrier to the spinosyn concentration of approximately 1000 ppm before applying the anti-lice formulation to the textile.

7. The method of claim 1, wherein the textile is a textile in need of treatment, the textile in need of treatment including at least one of natural fibers and synthetic fibers.

8. The method of claim 1, further comprising, after applying the anti-lice formulation to the textile:

allowing the anti-lice formulation to dry on the textile without removing the anti-lice formulation from the textile.

9. An anti-lice formulation comprising:

an effective amount of a spinosyn, the spinosyn being present in the anti-lice formulation in an amount of approximately 1000 ppm; and a non-organic carrier, the anti-lice formulation being at least one of a suspension and a solution, the anti-lice formulation being active against all life-cycle stages of human lice and causing 100% mortality in human lice adults, immatures, and eggs when applied to a textile.

10. The anti-lice formulation of claim 9, wherein the anti-lice formulation is configured to be applied to a textile in need of treatment and to dry on the textile in need of treatment without changing a quality of the textile in need of treatment.

11. The anti-lice formulation of claim 10, wherein the textile in need of treatment includes at least one of natural fibers and synthetic fibers.

12. The anti-lice formulation of claim 9, wherein the spinosyn is at least one of a spinosad and a physiologically acceptable salt of a spinosyn.

13. The anti-lice formulation of claim 9, further comprising at least one additional active ingredient, the at least one additional active ingredient being at least one avermectin.

14. The anti-lice formulation of claim 9, wherein the anti-lice formulation is a liquid formulation, the liquid formulation being at least one of an aqueous suspension and an aqueous solution.

15. The anti-lice formulation of claim 9, wherein the anti-lice formulation is at least one of a wettable powder, a gel, a paste, a lotion, a foam, and a spray.

16. A method of producing an anti-lice formulation, the method comprising:

adding an amount of spinosyn to a non-organic carrier to produce at least one of an aqueous suspension and an aqueous solution in which the spinosyn is present in a concentration of approximately 1000 ppm.

* * * * *